United States Patent
Kuboi

(10) Patent No.: US 11,094,093 B2
(45) Date of Patent: Aug. 17, 2021

(54) COLOR PROCESSING PROGRAM, COLOR PROCESSING METHOD, COLOR SENSE INSPECTION SYSTEM, OUTPUT SYSTEM, COLOR VISION CORRECTION IMAGE PROCESSING SYSTEM, AND COLOR VISION SIMULATION IMAGE PROCESSING SYSTEM

(71) Applicant: MITSUI CHEMICALS, INC., Tokyo (JP)

(72) Inventor: Hironori Kuboi, Ogori (JP)

(73) Assignee: MITSUI CHEMICALS, INC., Tokyo (JP)

( * ) Notice: Subject to any disclaimer, the term of this patent is extended or adjusted under 35 U.S.C. 154(b) by 159 days.

(21) Appl. No.: 16/500,840

(22) PCT Filed: Apr. 27, 2018

(86) PCT No.: PCT/JP2018/017280
§ 371 (c)(1),
(2) Date: Oct. 4, 2019

(87) PCT Pub. No.: WO2018/207675
PCT Pub. Date: Nov. 15, 2018

(65) Prior Publication Data
US 2020/0098146 A1    Mar. 26, 2020

(30) Foreign Application Priority Data
May 10, 2017   (JP) .............................. JP2017-093897

(51) Int. Cl.
*G06T 11/00*    (2006.01)
*G06T 7/90*    (2017.01)

(52) U.S. Cl.
CPC .............. *G06T 11/001* (2013.01); *G06T 7/90* (2017.01)

(58) Field of Classification Search
CPC ........... G06T 11/001; G06T 7/90; G06T 1/20; H04N 1/6002; A61B 3/066
See application file for complete search history.

(56) References Cited

U.S. PATENT DOCUMENTS

2005/0105796 A1    5/2005  Hong et al.
2008/0193011 A1*   8/2008  Hayashi .................... G06T 1/00
                                                                        382/167

(Continued)

FOREIGN PATENT DOCUMENTS

EP            1816599 A1      8/2007
JP        2014-160391 A       9/2014

OTHER PUBLICATIONS

Jul. 24, 2018 International Search Report issued in International Patent Application No. PCT/JP2018/017280.

(Continued)

*Primary Examiner* — Christopher Wait
(74) *Attorney, Agent, or Firm* — Oliff PLC

(57) ABSTRACT

A computer is caused to execute processing of transforming a first color information indicating a first color in a first color space into a second color information in a second color space which is an opponent color space different from the first color space, according to a type of a color vision and a color vision strength indicating a degree of the color vision; calculating, in the second color space, a third color information having a predetermined color difference with respect to the transformed second color information; and transforming the calculated third color information into a fourth color information indicating a second color in the first color space, according to a type of a color vision and a color vision strength indicating a degree of the color vision.

13 Claims, 8 Drawing Sheets

(56) References Cited

U.S. PATENT DOCUMENTS

2014/0233070 A1   8/2014   Kishimoto
2014/0270516 A1   9/2014   Wang et al.

OTHER PUBLICATIONS

S. Lee Guth et al. "Vector Model for Normal and Dichromatic Color Vision" J. Opt. Soc. Am., vol. 70, No. 2, Feb. 1980, pp. 197-212.
Dec. 15, 2020 Search Report issued in European Patent Application No. 18798666.6.
P Capilla et al. "Looking for the Dichromatic Version of a Colour Vision Model". Journal of Optics A: Pure and Applied Optics, Institute of Physics Publishing, Bristol, GB, vol. 6, No. 9, Sep. 1, 2004, pp. 906-919.

* cited by examiner

COLOR PROCESSING PROGRAM, COLOR PROCESSING METHOD, COLOR SENSE INSPECTION SYSTEM, OUTPUT SYSTEM, COLOR VISION CORRECTION IMAGE PROCESSING SYSTEM, AND COLOR VISION SIMULATION IMAGE PROCESSING SYSTEM

CROSS REFERENCE TO RELATED APPLICATION

This application is a U.S. National Stage application claiming the benefit of prior filed International Application Number PCT/JP2018/017280, filed on Apr. 27, 2018, in which the International Application claims priority from Japanese Patent Application Number 2017-093897, filed on May 10, 2017, the entire contents of which are incorporated herein by reference.

TECHNICAL FIELD

The present invention relates to a color processing program, a color processing method, a color sense inspection system, an output system, a color vision correction image processing system, and a color vision simulation image processing system.

BACKGROUND ART

There has been proposed a technique of executing color processing on colors of an image to be displayed on a display such as an LCD (Liquid Crystal Display) and colors to be printed on a material such as paper according to a person with a color-vision disability.

For example, there has been proposed a technique of calculating color vision parameters based on a distribution of head-count of the level of color vision according to the type of color vision, selecting one of a plurality of color transformation tables from the calculated color vision parameters, and executing color transformation on an image using the selected color transformation table (refer to, for example, Patent Document 1).

Patent Document 1: Japanese Unexamined Patent Application Publication No. 2014-160391

DISCLOSURE

Problems to be Solved

Conventionally, the color transformation is executed with reference to one level of color vision such as the level of the color vision at which the head-count is largest in the distribution of head-count. However, the color vision has a large difference among individuals, so that it is conventionally difficult to execute the color transformation according to all types of color vision and levels of color vision.

The present invention has a proposition to provide a color processing program, a color processing method, a color sense inspection system, an output system, a color vision correction image processing system, and a color vision simulation image processing system, which can execute color processing according to a type of color vision and a level of color vision.

Means for Solving the Problems

A first invention is a color processing program causing a computer to execute processing of transforming a first color information indicating a first color in a first color space into a second color information in a second color space which is an opponent color space different from the first color space, according to a type of a color vision and a color vision strength indicating a degree of the color vision; calculating, in the second color space, a third color information having a predetermined color difference with respect to the transformed second color information; and transforming the calculated third color information into a fourth color information indicating a second color in the first color space, according to a type of a color vision and a color vision strength indicating a degree of the color vision.

A second invention is the color processing program according to the first invention, the processing further including processing of acquiring determination information indicating a result of determination by a subject of whether the first color and the second color are different or not, in which the processing of transforming into the fourth color information transforms the third color information into the fourth color information by changing the color vision strength according to the determination information.

A third invention is the color processing program according to the first invention or the second invention, in which the processing of calculating the third color information calculates the third color information by changing at least one component of a plurality of components included in the second color information.

A fourth invention is the color processing program according to any one of the first invention to the third invention, in which the second color space is an ATD space.

A fifth invention is the color processing program according to the fourth invention, in which the processing of calculating the third color information calculates the third color information by changing at least a T component or a D component of an A component, the T component, and the D component which are included in the second color information.

A sixth invention is a color processing method, including transforming a first color information indicating a first color in a first color space into a second color information in a second color space which is an opponent color space different from the first color space, according to a type of a color vision and a color vision strength indicating a degree of the color vision; calculating, in the second color space, a third color information having a predetermined color difference with respect to the transformed second color information; and transforming the calculated third color information into a fourth color information indicating a second color in the first color space, according to a type of a color vision and a color vision strength indicating a degree of the color vision.

A seventh invention is the color processing method according to the sixth invention, in which the second color space is an ATD space.

An eighth invention is a color sense inspection system, including a processing device executing processing of transforming a first color information indicating a first color in a first color space into a second color information in a second color space which is an opponent color space different from the first color space, according to a type of a color vision and a color vision strength indicating a degree of the color vision; calculating, in the second color space, a third color information having a predetermined color difference with respect to the transformed second color information; and transforming the calculated third color information into a fourth color information indicating a second color in the first color space, according to a type of a color vision and a color vision strength indicating a degree of the color vision; an output device outputting the first color and the second color in contrast to each other; and an input device accepting a result of a determination of a comparison between the first color and the second color by a subject.

A ninth invention is the color sense inspection system according to the eighth invention, in which the second color space is an ATD space.

A tenth invention is an output system, including a processing device executing processing of transforming a first color information indicating a first color in a first color space into a second color information in a second color space which is an opponent color space different from the first color space, according to a first type of a color vision and a first color vision strength indicating a degree of the color vision; and transforming the second color information into a third color information indicating a second color in the first color space, according to a second type of a color vision and a second color vision strength; and an output device outputting the second color in place of the first color.

An eleventh invention is the output system according to the tenth invention, in which 1) the first type and the second type are different and the first color vision strength and the second color vision strength are different, 2) the first type and the second type are the same and the first color vision strength and the second color vision strength are different, or 3) the first type and the second type are different and the first color vision strength and the second color vision strength are the same.

A twelfth invention is the output system according to the tenth invention or the eleventh invention, in which information indicating a person with a normal color vision is used for the first type and the first color vision strength or the second type and the second color vision strength.

A thirteenth invention is the output system according to any one of the tenth invention to the twelfth invention, in which the first type and the first color vision strength or the second type and the second color vision strength are information indicating the subject subjected to an inspection of a color sense using the color sense inspection system according to the eighth invention or the ninth invention.

A fourteenth invention is the output system according to any one of the tenth invention to the thirteenth invention, in which the second color space is an ATD space.

A fifteenth invention is a color vision correction image processing system, including the output system according to any one of the tenth invention to the fourteenth invention.

A sixteenth invention is a color vision simulation image processing system, including the output system according to any one of the tenth invention to the fourteenth invention.

The present invention can execute color processing according to a type of color vision and a level of color vision.

DETAILED DESCRIPTION OF THE EMBODIMENTS

Hereinafter, embodiments will be explained using the drawings.

Figure 1:
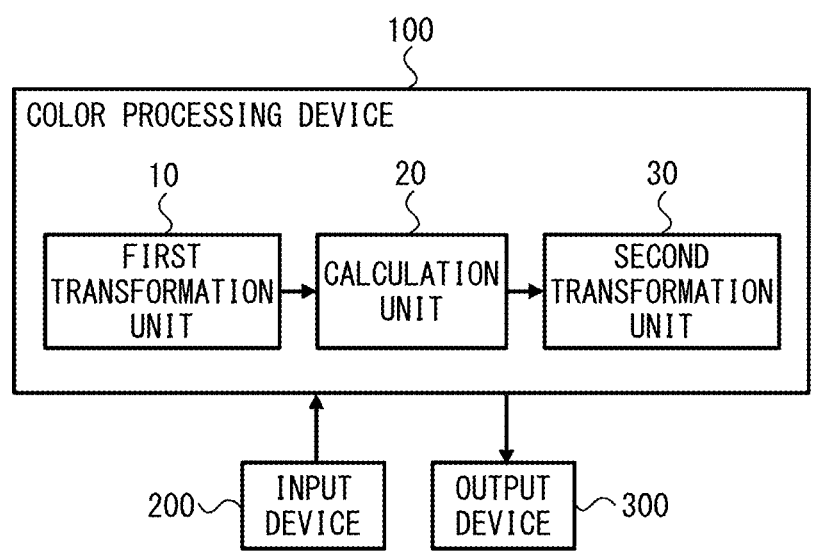
FIG. 1 is a diagram illustrating an embodiment of a color processing device.

FIG. 1 illustrates an embodiment of a color processing device.

A color processing device 100 illustrated in FIG. 1 is, for example, a computer device having a processor such as a CPU (Central Processing Unit) and a memory such as a hard disk device. Further, the color processing device 100 is connected to an input device 200 and an output device 300 via wire or radio.

The input device 200 is, for example, a mouse, a keyboard, a touch panel or the like, and accepts an input instruction from a person operating the color processing device 100, and outputs the accepted input instruction to the color processing device 100.

The output device 300 is, for example, a display, a printer or the like, and displays or prints data on an image or the like processed by the color processing device 100.

The color processing device 100 operates as a first transformation unit 10, a calculation unit 20, and a second transformation unit 30 by the processor of the computer device executing a color processing program stored in the memory.

The first transformation unit 10 transforms tristimulus values in an XYZ color system indicating a color input through the input device 200 into an A component, a T component, and a D component (hereinafter, called also as "ATD components") in an ATD color space indicating a color space of a human optic nerve layer, according to the type of color vision and the color vision strength indicating the degree of color vision. Note that the ATD color space is a three-dimensional space made of a brightness coordinate A and opponent color coordinates T and D. Further, the type of color vision and the color vision strength in the first transformation unit 10 may be set in advance using the input device 200, or may be input together with the tristimulus values of a color through the input device 200. The operation of the first transformation unit 10 will be explained in FIG. 2.

Note that the type of color vision and the color vision strength may be input together with the tristimulus values of a color through the input device 200, or may be set in advance. Further, the color to be input is not limited to the XYZ color system but may be data in an sRGB color system, an L*a*b* color system, an L*u*v* color system or the like.

The calculation unit 20 calculates the ATD components in the ATD color space having a predetermined color difference with respect to the ATD components transformed by the first transformation unit 10. Note that it is preferable that the predetermined color difference is appropriately decided according to the application destination of the color processing device 100. For example, when the color processing device 100 operates as a color sense inspection system in cooperation with the input device 200 and the output device 300, the predetermined color difference is set to a value of "1" or the like. Further, when the color processing device 100 cooperates with the input device 200 and the output device 300 as a color vision simulation image processing system which simulates the color vision according to the type of color vision and the color vision strength, the predetermined color difference is set to a value of "0". Further, when the color processing device 100 cooperates with the input device 200 and the output device 300 as an output system or a color vision correction image processing system which adjusts the color scheme or the like according to the type of color vision and the color vision strength for an image, a map or the like to be displayed or printed on the output device 300, the predetermined color difference is set to a value of "0".

Note that when the predetermined color difference is set to "0", the calculation unit 20 may be omitted. The operation of the calculation unit 20 will be explained in FIG. 3.

The second transformation unit 30 transforms the ATD components calculated by the calculation unit 20 into the tristimulus values in the XYZ color system according to the type of color vision and the color vision strength different from those in the first transformation unit 10. Note that the type of color vision and the color vision strength in the second transformation unit 30 may be set in advance using the input device 200, or may be input together with the tristimulus values of a color through the input device 200.

The color processing device 100 then executes color adjustment such as sRGB according to the output device 300 on the tristimulus values transformed by the second transformation unit 30, and outputs the tristimulus values to the output device 300.

Figure 2:
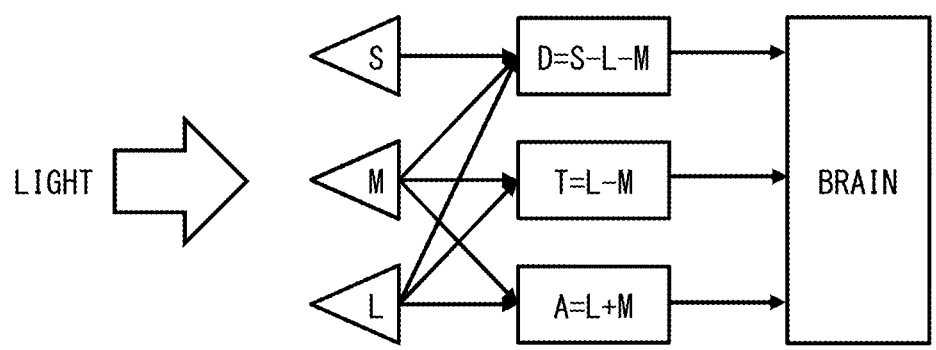
FIG. 2 is a diagram illustrating an example of a principle of a color vision of a human.

FIG. 2 illustrates an example of the principle of color vision of a human. FIG. 2 illustrates, for example, a color vision model of S. L. Guth, R. W. Massof, and T. Benzschawel, "Vector model for normal and dichromatic color vision", J. Opt. Soc. Am., 70, pp. 197-212 (1980) (hereinafter, called also as a "Guth's color vision model").

As illustrated in FIG. 2, the human eye has three such as L-cone, M-cone, and S-cone having sensitivities to wavelengths of light different from one another in the retina, and detects incident light. The L-cone has a sensitivity to light near the wavelengths of greenish yellow to red, the M-cone has a sensitivity to light near the wavelengths of green to orange, and the S-cone has a sensitivity to light near the wavelengths of purple to blue. The L-cone, the M-cone, and the S-cone output signals corresponding to the detected intensities of light respectively.

In the Guth's color vision model, a ganglion cell of the eye calculates the ATD components in the ATD color space using the signal output from each of the L-cone, the M-cone and the S-cone. For example, the ganglion cell calculates a value obtained by adding the intensity of light detected by the L-cone and the intensity of light detected by the M-cone, namely, the brightness of light, as the A component. Further, the ganglion cell calculates a value obtained by subtracting the intensity of light detected by the M-cone from the intensity of light detected by the L-cone, as the T component. Further, the ganglion cell calculates a value obtained by subtracting the intensities of light detected by the L-cone and the M-cone from the intensity of light detected by the S-cone, as the D component. The ganglion cell then outputs the calculated A component as a luminance signal and the D component and the T component as color signals, to the brain. The brain then recognizes the color and the brightness of a viewing object, based on the received ATD components.

Note that at least one cone of the L-cone, the M-cone, and the S-cone is absent or does not normally function in some cases. For example, a person whose L-cone is absent or does not normally function is classified into a type 1 dichromacy or a type 1 trichromacy having difficulty in discriminating red from green. Besides, a person whose M-cone is absent or does not normally function is classified into a type 2 dichromacy or a type 2 trichromacy having difficulty in discriminating red from green. Besides, a person whose S-cone is absent or does not normally function is classified into a type 3 dichromacy or a type 3 trichromacy having difficulty in discriminating blue from yellow. Hereinafter, the type 1 dichromacy and the type 1 trichromacy are called also as "P (Protanope) type color vision", the type 2 dichromacy and the type 2 trichromacy are called also as "D (Deuteranope) type color vision", and the type 3 dichromacy and the type 3 trichromacy are called also as "T (Tritanope) type color vision".

In the color processing device 100 illustrated in FIG. 1, tristimulus values X, Y, Z in the XYZ color system and the ATD components in the ATD color space are related as in Expression (1) based on the Guth's color vision model.

$$\begin{pmatrix} A \\ T \\ D \end{pmatrix} = mHKM \begin{pmatrix} X' \\ Y' \\ Z' \end{pmatrix} \quad (1)$$

$$\left[ \begin{pmatrix} X' \\ Y' \\ Z' \end{pmatrix} = M^{-1}K^{-1}H^{-1}m^{-1} \begin{pmatrix} A \\ T \\ D \end{pmatrix} \right]$$

Note that tristimulus values X', Y', Z' indicate the tristimulus values X, Y, Z subjected to Judd transformation. M represents a 3×3 matrix which transforms the tristimulus values X', Y', Z' into tristimulus values L, M, S in an LMS color space, and is expressed, for example, as in Expression (2).

$$M = \begin{pmatrix} 0.2435 & 0.8524 & -0.0516 \\ -0.3954 & 1.1642 & 0.0837 \\ 0 & 0 & 0.6225 \end{pmatrix} \quad (2)$$

K represents a 3×3 matrix which executes, for example, white color correction in white illumination light such as D65 based on the chromatic adaptation theory by von Kries. H represents a 3×3 matrix which performs transformation into an opponent color response to the optic nerve layer, and, for example, Expression (3) to Expression (6) defined for each type of color vision are used so that the A component and the Y component indicating luminance are proportional to each other.

$$H_C = \begin{pmatrix} 0.5952 & 0.3666 & 0.0001 \\ 0.9552 & -1.2835 & 0 \\ -0.0250 & 0.0001 & 0.0483 \end{pmatrix} \quad (3)$$

$$H_P = \begin{pmatrix} 0 & 0.9621 & 0 \\ 0 & 0 & 0 \\ 0 & -0.0400 & 0.0483 \end{pmatrix} \quad (4)$$

$$H_D = \begin{pmatrix} 0.9621 & 0 & 0 \\ 0 & 0 & 0 \\ -0.0400 & 0 & 0.0483 \end{pmatrix} \quad (5)$$

$$H_T = \begin{pmatrix} 0.5967 & 0.3654 & 0 \\ 0.9553 & -1.2836 & 0 \\ 0 & 0 & 0 \end{pmatrix} \quad (6)$$

Note that it is preferable that H of each type of color vision is not limited to the matrix having components shown in Expression (3) to Expression (6), but is appropriately decided according to the situation in which the color processing device 100 is applied.

Further, m represents a coefficient to be adjusted according to various visual perception phenomena, and represents a 3×3 matrix which is expressed, for example, as in Expression (7) so as to correspond to a perception phenomenon of brightness at a supraliminal level.

$$m = \begin{pmatrix} 0.75 & 0 & 0 \\ 0 & 1 & 0 \\ 0 & 0 & 6 \end{pmatrix} \quad (7)$$

Note that each of $H_P$ of the P-type color vision, $H_D$ of the D-type color vision, and $H_T$ of the T-type color vision shown in Expression (4) to Expression (6) represents H when the L-cone, the M-cone, or the S-cone is absent, namely, the symptom of color vision is most serious. However, the symptom of color vision varies according to the degree at which each cone is absent or does not normally function and therefore has a large difference among individuals. For this reason, even if H in one of Expression (3) to Expression (6) is applied to the person of the P-type color vision, the D-type color vision, or the T-type color vision, it is difficult to reproduce the way of viewing in all color visions.

Hence, to reproduce the way of viewing in all color visions, Hs in the P-type color vision, the D-type color vision, and the T-type color vision are defined as in Expression (8) to Expression (10).

$$H = k_P H_P + (1 - k_P) H_C \quad (8)$$

$$H = k_D H_D + (1 - k_D) H_C \quad (9)$$

$$H = k_T H_T + (1 - k_T) H_C \quad (10)$$

Note that $k_P$, $k_D$, and $k_T$ indicate respective color vision strengths of the P-type color vision, the D-type color vision, and the T-type color vision, and are set to values in a range of 0 to 1. In other words, as shown in Expression (8) to Expression (10), each color vision of the P-type color vision, the D-type color vision, and the T-type color vision is expressed by weighted addition of the P-type color vision, the D-type color vision, or the T-type color vision due to absence of the L-cone, the M-cone, or the S-cone and the color vision of a person with a normal color vision.

Figure 3:
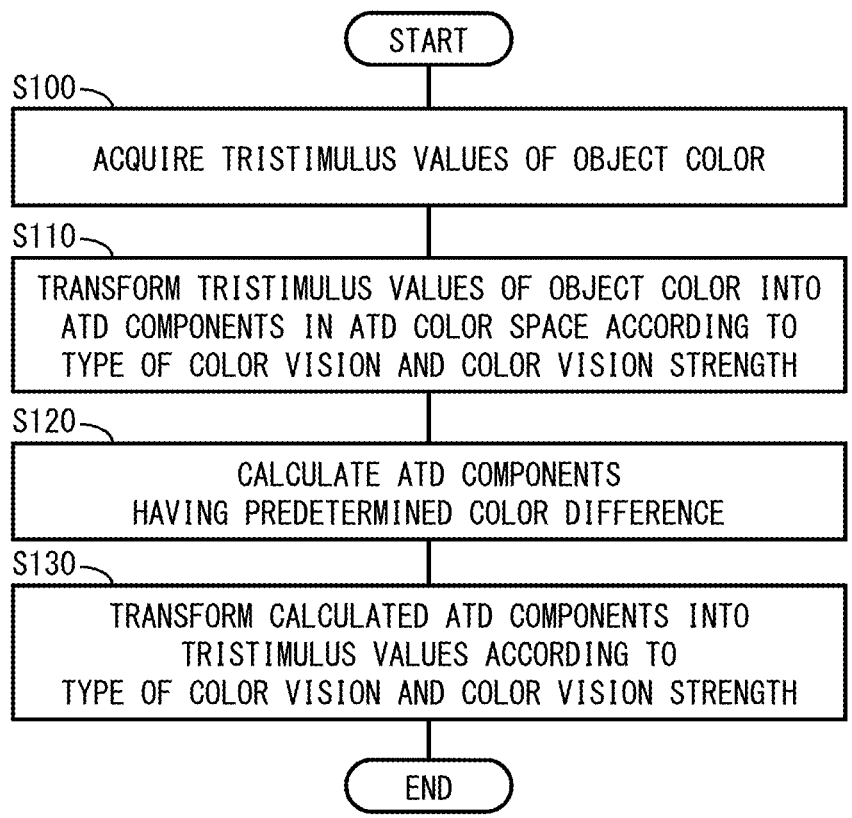
FIG. 3 is a chart illustrating an example of color processing in the color processing device illustrated in FIG. 1.

FIG. 3 illustrates an example of color processing in the color processing device 100 illustrated in FIG. 1. The processing illustrated in FIG. 3 is realized by the color processing device 100 executing the color processing program. In short, FIG. 3 illustrates embodiments of the color processing program and a color processing method. Note that the processing illustrated in FIG. 3 may be realized by hardware installed in the color processing device 100. In this case, the first transformation unit 10, the calculation unit 20, and the second transformation unit 30 illustrated in FIG. 1 are realized by a circuit arranged in the color processing device 100.

At Step S100, the first transformation unit 10 acquires, through the input device 200, the tristimulus values X, Y, Z in the XYZ color system indicating a color to be processed (hereinafter, called also as an "object color").

Next, at Step S110, the first transformation unit 10 Judd-transforms the tristimulus values X, Y, Z of the object color acquired at Step S100 to obtain Judd-transformed tristimulus values X', Y', Z'. The first transformation unit 10 then transforms the Judd-transformed tristimulus values X', Y', Z' of the object color into ATD components in the ATD color space using one of Expression (8) to Expression (10) according to the type of color vision and the color vision strength and using Expression (1).

Note that when transforming the tristimulus values X, Y, Z of the object color into the ATD components, the first transformation unit 10 Judd-transforms the tristimulus values X, Y, Z of the object color, but the Judd transformation may be omitted.

Next, at Step S120, the calculation unit 20 calculates ATD components having a predetermined color difference with reference to the ATD components of the object color transformed at Step S110.

Here, a color difference ΔE between two ATD components (A1, T1, D1) and (A2, T2, D2) in the ATD color space is found by integration along a geodesic line between the two ATD components as in Expression (11).

$$\Delta E = \int_{(A1,T1,D1)}^{(A2,T2,D2)} \quad (11)$$

$$dE = \sqrt{\left(\ln\frac{r_2}{r_1}\right)^2 + \theta^2}$$

dE represents a small distance on the geodesic line and is expressed by $(dA^2 + dT^2 + dD^2)^{1/2}/r$. $r_1$ and $r_2$ represent lengths of a vector of the ATD components (A1, T1, D1) and a vector of the ATD components (A2, T2, D2). r represents a distance from the origin (0, 0, 0) to the ATD components (A, T, D). θ represents an angle (radian) formed between the vector of the ATD components (A1, T1, D1) and the vector of the ATD components (A2, T2, D2).

Then, by standardizing Expression (11) by a threshold value, the color difference ΔE is expressed as in Expression (12). Note that W represents Weber fraction and is set to a value of 0.01 or the like.

$$\Delta E = \sqrt{\left(\ln\frac{r_2}{r_1}\right)^2 + \theta^2} / \ln(1 + W) \quad (12)$$

The calculation unit 20 calculates, using Expression (12), the ATD components (A2, T2, D2) having a color difference ΔE that is a predetermined color difference (for example, ΔE=1 or the like) when the ATD components (A1, T1, D1) are set as the ATD components of the object color.

Note that when the predetermined color difference is set to "0", the processing at Step S120 may be omitted.

Next, at Step S130, the second transformation unit 30 transforms the ATD components (A2, T2, D2) calculated at Step S120 into tristimulus values in the XYZ color system, using the same type of color vision and color vision strength as those at Step S110 and using Expression (1). The color processing device 100 executes color adjustment such as sRGB according to the output device 300 on the tristimulus values transformed by the second transformation unit 30, and outputs the tristimulus values to the output device 300. The color processing device 100 then ends the color processing.

In the above embodiment illustrated in FIG. 1 to FIG. 3, the color processing device 100 performs weighted addition of the color vision of the P-type color vision, the D-type color vision, or the T-type color vision and the color vision of the person with a normal color vision using the color vision strength of each of the P-type color vision, the D-type color vision, and the T-type color vision and thereby expresses the color vision of a person by Expression (8) to Expression (10). Thus, the color processing device 100 can execute the color processing according to the type of color vision and the color vision strength with higher accuracy than before.

Figure 4:
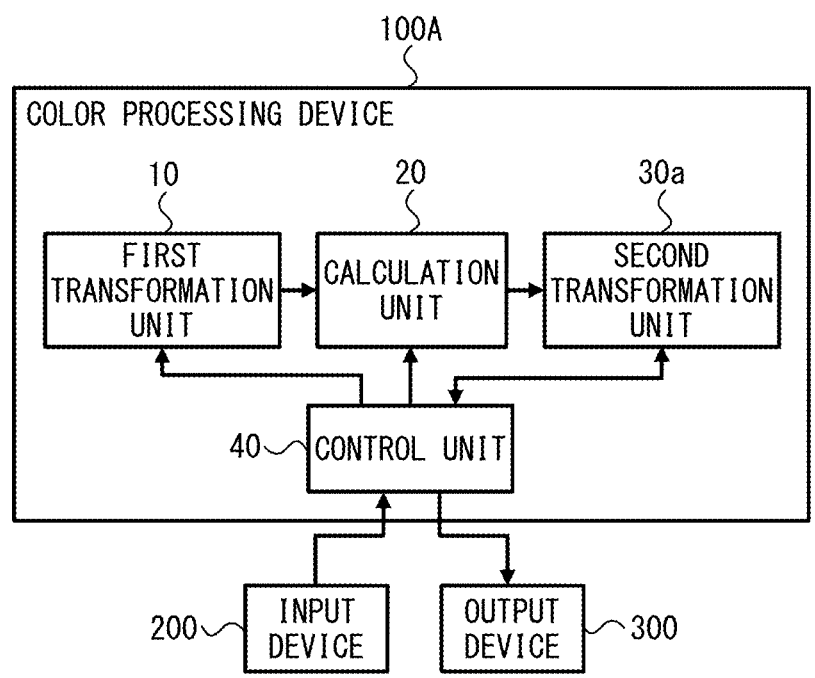
FIG. 4 is a diagram illustrating another embodiment of the color processing device.

FIG. 4 illustrates another embodiment of the color processing device. The identical or similar numerals and symbols are given to elements having the identical or similar functions to those of the elements explained in FIG. 1, and detailed explanation of those elements will be omitted.

A color processing device 100A illustrated in FIG. 4 is, for example, a computer device having a processor such as a CPU and a memory such as a hard disk device. Further, the color processing device 100A is connected to an input device 200 and an output device 300 via wire or radio. Further, the color processing device 100A operates as a color sense inspection system, in cooperation with the input device 200 and the output device 300.

The color processing device 100A operates as a first transformation unit 10, a calculation unit 20, a second transformation unit 30a, and a control unit 40 by the processor of the computer device executing a color processing program stored in the memory.

The first transformation unit 10 transforms tristimulus values in an XYZ color system of a color input through the input device 200 and the control unit 40 into ATD components in an ATD color space, according to the type of color vision and the color vision strength. Note that when the color processing device 100A operates as a color vision correction image processing system, the color vision of a person with a normal color vision is used as a reference, and therefore the person with a normal color vision is set as the type of color vision in the first transformation unit 10 and "0" indicating the person with a normal color vision is set as color vision strengths $k_P$, $k_D$, $k_T$.

The calculation unit 20 calculates the ATD components in the ATD color space having a predetermined color difference with respect to the ATD components transformed by the first transformation unit 10.

The second transformation unit 30a transforms the ATD components calculated by the calculation unit 20 into the tristimulus values in the XYZ color system based on the type of the P-type color vision, the D-type color vision, or the T-type color vision which is set in advance through the input device 200 and on the color vision strength adjusted by the control unit 40 according to a color sense inspection. Note that at the start time of the color processing, the type of color vision and the color vision strength of a subject are unknown, and therefore one type of the P-type color vision, the D-type color vision, or the T-type color vision is set and arbitrary values in a range of 0 to 1 are set as initial values of color vision strengths $k_P$, $k_P$, and $k_T$ in the second transformation unit 30a. Note that when the color processing device 100A operates as a color vision simulation image processing system, the color vision of a person with a normal color vision is used as a reference, and therefore the person with a normal color vision is set as the type of color vision in the second transformation unit 30a and "0" indicating the person with a normal color vision is set as the color vision strengths $k_P$, $k_D$, $k_T$.

The control unit 40 controls the operations of the units of the color processing device 100A. For example, the control unit 40 executes color adjustment such as sRGB according to the output device 300 on data of the tristimulus values of the color input from the input device 200 and the tristimulus values of the color transformed by the second transformation unit 30a. The control unit 40 then outputs the color-adjusted data to the output device 300. Further, the control unit 40 changes the color vision strength according to an input instruction from the input device 200, and outputs the changed color vision strength to the second transformation unit 30a. Further, the control unit 40 controls transmission and reception of the data between the input device 200 and output device 300, and, the color processing device 100A.

Figure 5:
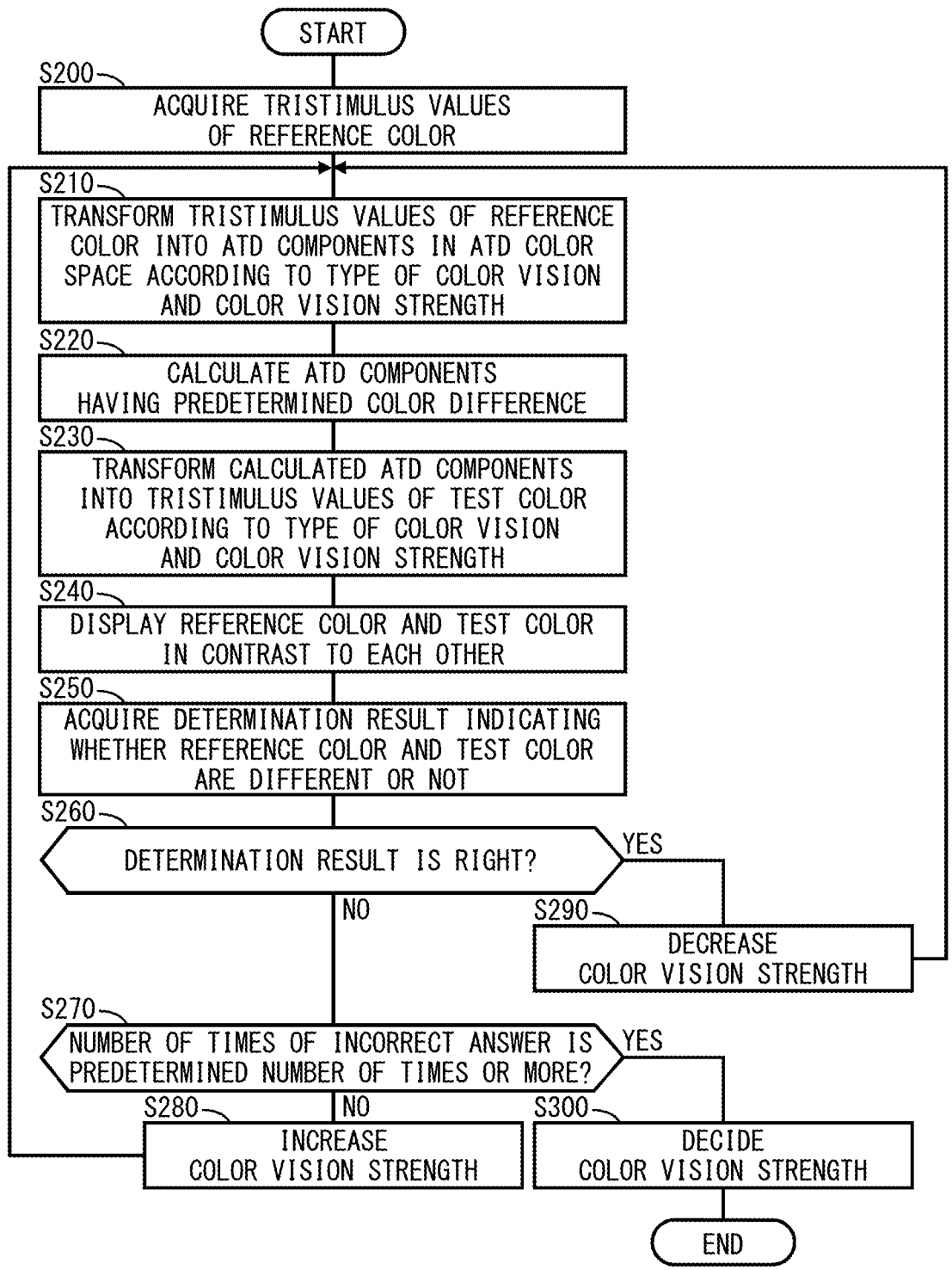
FIG. 5 is a chart illustrating an example of color processing in the color processing device illustrated in FIG. 4.

FIG. 5 illustrates an example of color processing in the color processing device 100A illustrated in FIG. 4. The processing illustrated in FIG. 5 is realized by the color processing device 100A executing the color processing program. In short, FIG. 5 illustrates other embodiments of the color processing program and the color processing method. Note that the processing illustrated in FIG. 5 may be realized by hardware installed in the color processing device 100A. In this case, the first transformation unit 10, the calculation unit 20, the second transformation unit 30a, and the control unit 40 illustrated in FIG. 4 are realized by a circuit arranged in the color processing device 100A.

Note that the processing illustrated in FIG. 5 will be explained for the case where the P-type color vision is inspected in a color sense inspection, and the same applies to the case where the D-type color vision or the T-type color vision is inspected.

At Step S200, the control unit 40 acquires, through the input device 200, the tristimulus values X, Y, Z in the XYZ color system indicating the object color which is a color used as a reference in the color sense inspection (hereinafter, called also as a "background color" or a "reference color"). The control unit 40 outputs the acquired tristimulus values X, Y, Z of the color to the first transformation unit 10. Note that the control unit 40 may acquire, through the input device 200, the type of color vision to be inspected together with the tristimulus values X, Y, Z of the reference color. In this case, the control unit 40 outputs the acquired type of color vision to the second transformation unit 30a.

Next, at Step S210, the first transformation unit 10 Judd-transforms the tristimulus values X, Y, Z of the reference color acquired at Step S200 to obtain tristimulus values X', Y', Z'. The first transformation unit 10 transforms the Judd-transformed tristimulus values X', Y', Z' of the reference color into ATD components in the ATD color space using Expression (8) of the type and the color vision strength set in advance and using Expression (1).

Next, at Step S220, the calculation unit 20 calculates, using Expression (12), ATD components (A2, T2, D2) having a color difference $\Delta E$ that is a predetermined color difference with respect to the ATD components (A1, T1, D1) of the reference color transformed at Step S210.

For example, in order to calculate the ATD components (A2, T2, D2), the calculation unit 20 changes the T component under the condition that A1=A2, D1=D2 and the color difference ΔE=1 (predetermined color difference) to find $r_2$ and θ satisfying the color difference ΔE=1. For example, $r_2$ and θ in Expression (12) are assumed to be functions F(T) and G(T) using the T component as a variable. The calculation unit 20 then executes a convergence calculation such as an iteration method of Steffensen while changing the T component to find $r_2$ and θ satisfying the color difference ΔE=1, namely, T2, to calculate the ATD components (A2, T2, D2). Note that the predetermined color difference may be a value other than 1.

Further, when the type of color vision is the D-type color vision, the calculation unit 20 preferably finds $r_2$ and θ satisfying the color difference ΔE=1 while changing the T component under the same condition as that in the case of the P-type color vision.

Further, when the type of color vision is the T-type color vision, the calculation unit 20 preferably finds $r_2$ and θ satisfying the color difference ΔE=1 while changing the D component under the condition that A1=A2, T1=T2, and the color difference ΔE=1.

Next, at Step S230, the second transformation unit 30a transforms the ATD components (A2, T2, D2) calculated at Step S220 into tristimulus values in the XYZ color system, using Expression (8) of the type of the P-type color vision and the color vision strength $k_P$ and using Expression (1). The control unit 40 then uses the color of the transformed tristimulus values as a test color and executes color adjustment such as sRGB according to the output device 300 on the tristimulus values of the reference color and the tristimulus values of the test color, and outputs data on the color-adjusted reference color and test color to the output device 300.

Next, at Step S240, the output device 300 receives the data on the reference color and the test color from the color processing device 100A, and displays the reference color and the test color in contrast to each other on a display such as an LCD.

Figure 6:
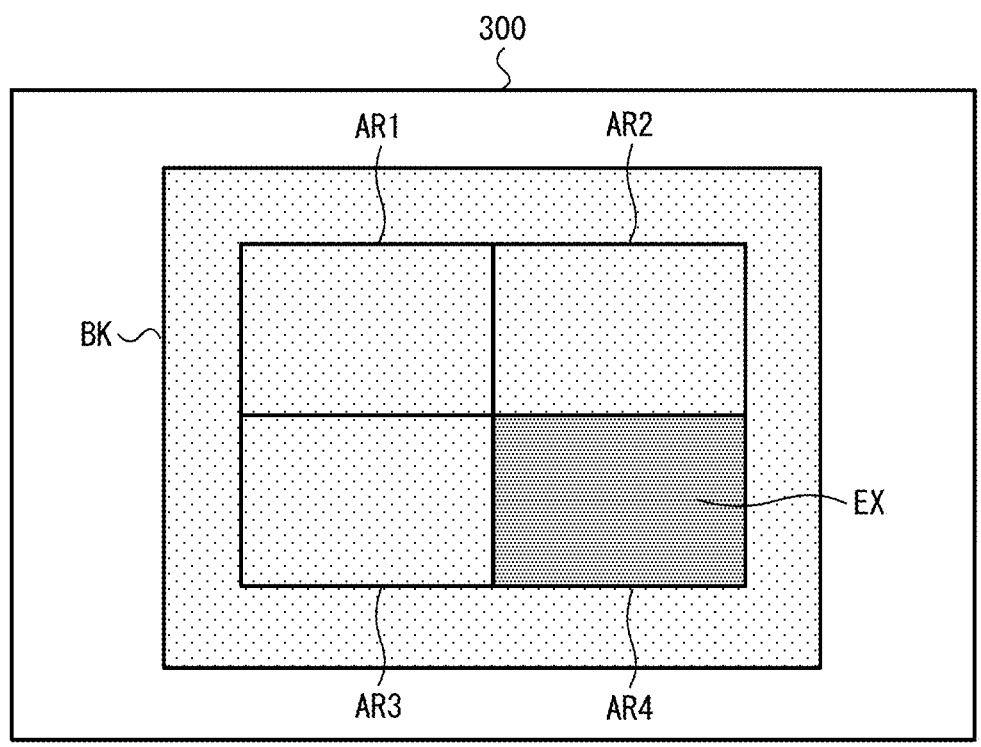
FIG. 6 is a chart illustrating an example of display of a reference color and a test color in an output device illustrated in FIG. 5.

FIG. 6 illustrates an example of display of the reference color and the test color in the output device 300 illustrated in FIG. 5. As illustrated in FIG. 6, the output device 300 displays the reference color illustrated by shading using a region BK including the center of the display such as the LCD as a background region, for example, based on a control instruction from the color processing device 100A. Further, the output device 300 sets four regions AR1 to AR4 of the region BK based on the control instruction from the color processing device 100A. The output device 300 then displays a test color EX illustrated by shading different from that of the reference color using one region AR4 of the four regions AR1 to AR4 as a test region. In short, the output device 300 displays the reference color using the regions AR1 to AR3 as a reference region.

Note that the output device 300 displays a peripheral color such as gray or white in a region (peripheral region) around the outside of the region BK, but may display another color. Further, the peripheral color preferably has a color such as gray and has the same luminance as that of the reference color or the like which prevents the subject from feeling glaring. However, the peripheral color is not limited to the above, but may have any color other than gray and may have luminance different from that of the reference color or the like.

Further, the test color EX may be displayed in any of the region AR1, the region AR2, and the region AR3, and may be displayed in a plurality of regions of the regions AR1 to AR4. In this case, the number of regions in which the test color EX is displayed is preferably smaller than the number of regions in which the test color EX is not displayed. Further, the four regions AR1 to AR4 are set in the region BK in which the reference color is displayed, but a plurality of, such as two or more, regions may be set. Further, the color displayed in the region BK excluding the regions AR1 to AR4 may be different from the reference color, may be an arbitrary color, and may be gray or white that is the same as that in the peripheral region.

Further, the output device 300 may set the regions AR1 to AR4 by separating them by a frame border having a predetermined width (for example, three pixels or the like). Thus, the subject can more accurately discriminate the color of each of the regions AR1 to AR4.

Further, the output device 300 sets the rectangular regions AR1 to AR4, but may set regions AR1 to AR4 having an arbitrary shape of the same size.

Further, the output device 300 may randomly arrange the regions AR1 to AR4 having the same size separately from one another. In this case, the output device 300 preferably arranges the regions AR1 to AR4 so that they come within the field of vision of the subject, and preferably arranges the regions AR1 to AR4 with the distances between the regions AR1 to AR4 constant. However, the output device 300 may arrange the regions AR1 to AR4 without limitation to the above.

Further, the output device 300 may display the reference color and the test color EX in each of the regions AR1 to AR4 with the same amount of noise added to them. This is because the sense of the luminance (an A-direction in the ATD space) to a color differs depending on a subject, so that making the luminance difficult to recognize due to the addition of the noise allows the subject to genuinely discriminate the color. Further, the output device 300 may add noise in a D-direction or the A-direction or in the D-direction and the A-direction in the case of discrimination in the T-direction, and may add noise in the T-direction or the A-direction or in the T-direction and the A-direction in the case of discrimination in the D-direction.

Next, at Step S250, the control unit 40 causes the subject to select, using the input device 200, a region in which the test color EX is displayed of the four regions AR1 to AR4. The control unit 40 then acquires data indicating the region selected by the subject from the input device 200 as a determination result indicating whether the reference color and the test color are different or not (namely, whether the reference color and the test color are distinguished or not).

Note that when the control unit 40 acquires the determination result, the input device 200 may be operated by the subject or may be operated by a medical worker or the like who performs the color sense inspection according to the response from the subject.

Next, at Step S260, the control unit 40 determines whether the determination result acquired at Step S250 is right or not (namely, whether the region AR4 in which the test color is displayed is selected or not in the case of FIG. 6). When the determination result is right, the processing by the color processing device 100A shifts to Step S290. On the other hand, when the determination result is not right, the control unit 40 increases the number of times of incorrect answer by one. In this case, the processing by the color processing device 100A shifts to Step S270.

At Step S270, the control unit 40 determines whether or not the number of times of incorrect answer is a predetermined value or larger. When the number of times of incorrect answer is smaller than the predetermined value, the processing by the color processing device 100A shifts to Step S280. On the other hand, when the number of times of incorrect answer is equal to or larger than the predetermined value, the processing by the color processing device 100A shifts to Step S300. Note that it is preferable that the predetermined value is appropriately decided according to the required accuracy or the like of the color sense inspection.

Next, at Step S280, when the determination result at Step S250 is not right, namely, the subject cannot distinguish the reference color from the test color, the control unit 40 increases the value of the color vision strength $k_P$. For example, the control unit 40 increases the value of the color vision strength $k_P$ at an interval of 0.1 or the like or an interval set in advance in a range of 0 to 1. The control unit 40 then outputs the increased value of the color vision strength $k_P$ to the second transformation unit 30a. In this case, the processing by the color processing device 100A shifts to Step S210.

At Step S290, when the determination result at Step S250 is right, namely, the subject can distinguish the reference color from the test color, the control unit 40 decreases the value of the color vision strength $k_P$. For example, the control unit 40 decreases the value of the color vision strength $k_P$ at an interval of 0.1 or the like or an interval set in advance in a range of 0 to 1. The control unit 40 then outputs the decreased value of the color vision strength $k_P$ to the second transformation unit 30a. In this case, the processing by the color processing device 100A shifts to Step S210.

At Step S300, the control unit 40 decides the color vision strength of the subject from the history of the changed $k_P$. Note that as the method of deciding $k_P$, a method of taking an average value at a halfway point by an up-and-down method or the like may be used, or a method of deciding $k_P$ from the distribution of a correct answer ratio of the result of randomly changing $k_P$ at Step S260 or the like may be used. The control unit 40 outputs the result of the inspection including the decided value of the color vision strength $k_P$ to the output device 300. The color processing device 100A then ends the color processing.

In the above embodiment illustrated in FIG. 4 to FIG. 6, the color processing device 100A expresses the color vision of a person by Expression (8) to Expression (10) by weighted addition of the color vision of the P-type color vision, the D-type color vision, or the T-type color vision and the color vision of the person with a normal color vision using the color vision strength of each of the P-type color vision, the D-type color vision, and the T-type color vision. Thus, the color processing device 100A can execute the color processing according to the type of color vision and the color vision strength with higher accuracy than before and can accurately decide the type of color vision and the color vision strength of the subject.

Figure 7:
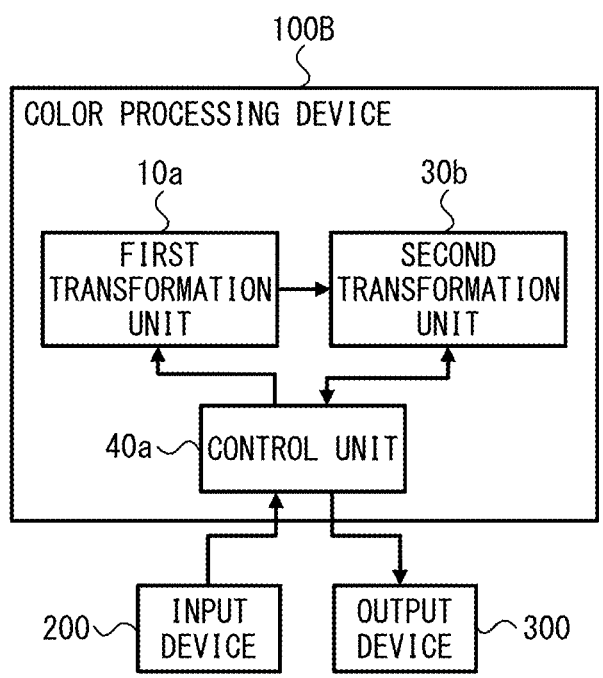
FIG. 7 is a diagram illustrating another embodiment of the color processing device.

FIG. 7 illustrates another embodiment of the color processing device. The identical or similar numerals and symbols are given to elements having the identical or similar functions to those of the elements explained in FIG. 1, and detailed explanation of those elements will be omitted.

A color processing device 100B illustrated in FIG. 7 is, for example, a computer device having a processor such as a CPU and a memory such as a hard disk device. Further, the color processing device 100B is connected to an input device 200 and an output device 300 via wire or radio. Further, the color processing device 100B operates as an output system, a color vision correction image processing system, or a color vision simulation image processing system, in cooperation with the input device 200 and the output device 300.

The color processing device 100B operates as a first transformation unit 10a, a second transformation unit 30b, and a control unit 40a by the processor of the computer device executing a color processing program stored in the memory. Note that when the color processing device 100B operates as the output system, the color vision correction image processing system, or the color vision simulation image processing system, the predetermined color difference is set to "0". Therefore, in the color processing device 100B illustrated in FIG. 7, the calculation unit 20 is omitted.

The first transformation unit 10a acquires, for example, through the input device 200 and the control unit 40a, data on a printed matter including sentences of color characters or the like and images, an image captured by a digital camera or the like, or a map used in navigation, or the like. The first transformation unit 10a transforms tristimulus values in an XYZ color system of a color included in the acquired data into ATD components in an ATD color space, according to the type of color vision and the color vision strength indicating the degree of color vision.

Note that, for example, when pixel values or the like of the image are given by RGB, the first transformation unit 10a preferably transforms RGB into the tristimulus values in the XYZ color system. Further, the type of color vision and the color vision strength in the first transformation unit 10a may be input using the input device 200. Further, the printed matter, image or the like may be acquired from an external device, a network or the like through an input/output interface and a network interface included in the color processing device 100B.

The second transformation unit 30b transforms the ATD components of the data on the image or the like transformed by the first transformation unit 10a into the tristimulus values in the XYZ color system according to the type of color vision and the color vision strength different from those in the first transformation unit 10a. Note that the type of color vision and the color vision strength in the second transformation unit 30b may be input using the input device 200.

The control unit 40a controls the operations of the units of the color processing device 100B. For example, the control unit 40a executes color adjustment such as sRGB according to the output device 300 on the tristimulus values of the color of the data on the image or the like transformed by the second transformation unit 30b, and outputs the color-adjusted data on the image or the like to the output device 300. Further, the control unit 40a controls transmission and reception of the data between the input device 200 and output device 300, and, the color processing device 100B.

Figure 8:
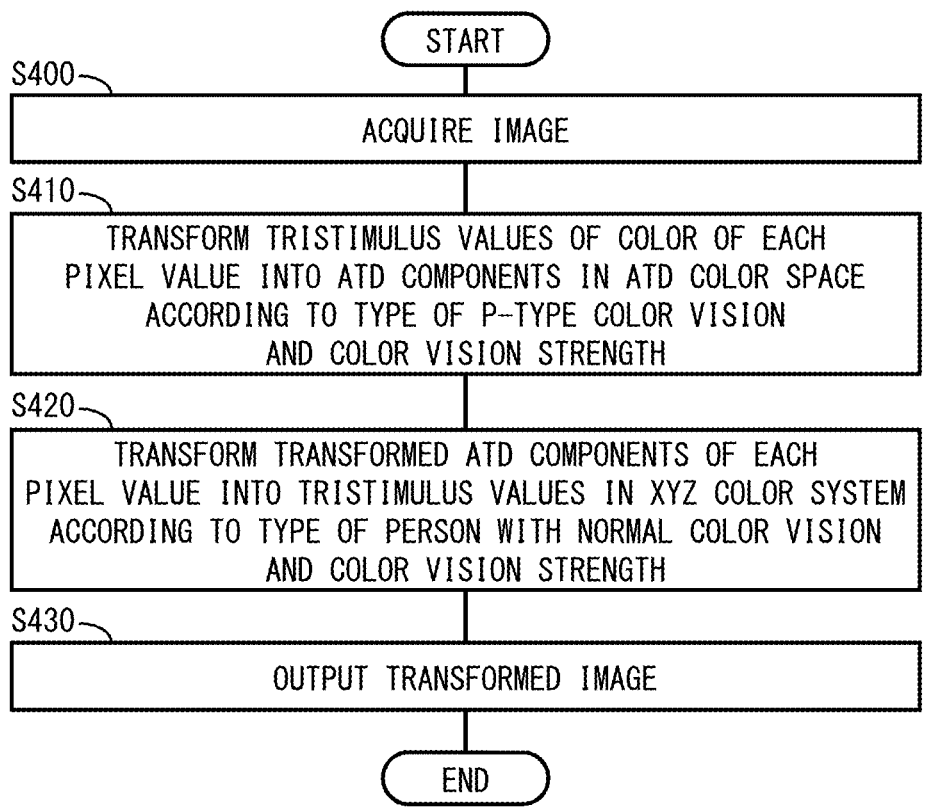
FIG. 8 is a chart illustrating an example of color processing in the color processing device illustrated in FIG. 7.

FIG. 8 illustrates an example of color processing in the color processing device 100B illustrated in FIG. 7. The processing illustrated in FIG. 8 is realized by the color processing device 100B executing the color processing program. In short, FIG. 8 illustrates other embodiments of the color processing program and the color processing method. Note that the processing illustrated in FIG. 8 may be realized by hardware installed in the color processing device 100B. In this case, the first transformation unit 10a, the second transformation unit 30b, and the control unit 40a illustrated in FIG. 7 are realized by a circuit arranged in the color processing device 100B.

Note that the processing illustrated in FIG. 8 will be explained for the case of an image, and the same applies to the case of a printed matter including color characters or the like, a map, or the like. Further, in the processing illustrated in FIG. 8, the case where transformation processing is executed so that when the person with a normal color vision views it, the person with a normal color vision senses the color difference sensed by a person of the P-type color vision will be explained. However, the processing illustrated in FIG. 8 applies to the case where transformation processing is executed so that when the person with a normal color vision views it, the person with a normal color vision senses the color difference sensed by a person of the D-type color vision or the T-type color vision, or to the case where transformation processing is executed so that when a person of the P-type color vision, the D-type color vision, or the T-type color vision views it, the person of the P-type color vision, the D-type color vision, or the T-type color vision senses the color difference sensed by the person with a normal color vision.

At Step S400, the control unit 40a acquires data on an image to be processed through the input device 200. The control unit 40a outputs the acquired data on the image or the like to the first transformation unit 10a. Note that the control unit 40a may acquire, together with the data on the image, the type of color vision and the color vision strength of a transformation source and the type of color vision and the color vision strength of a transformation destination through the input device 200. In this case, the control unit 40a outputs the acquired data on the image, and the acquired type of color vision and color vision strength of the transformation source to the first transformation unit 10a, and outputs the acquired type of color vision and color vision strength of the transformation destination to the second transformation unit 30b.

Next, at Step S410, the first transformation unit 10a Judd-transforms the tristimulus values X, Y, Z of each pixel value of the image acquired at Step S400 to obtain tristimulus values X', Y', Z'. The first transformation unit 10a transforms the Judd-transformed tristimulus values X', Y', Z' of each pixel value into ATD components in the ATD color space using Expression (8) of the type of the P-type color vision and the color vision strength $k_P$ as the transformation source and using Expression (1).

Note that when transforming the tristimulus values X, Y, Z of the object color into the ATD components, the first transformation unit 10a Judd-transforms the tristimulus values X, Y, Z of the object color, but the Judd-transformation may be omitted.

Next, at Step S420, the second transformation unit 30b transforms the ATD components of each pixel value transformed at Step S410 into tristimulus values in the XYZ color system, using Expression (8) corresponding to the type of color vision and the color vision strength $k_P$ of the person with a normal color vision as the color vision of the transformation destination and using Expression (1).

At Step S430, the control unit 40a executes color adjustment such as sRGB according to the output device 300 on the tristimulus values of the image transformed at Step S420, and outputs the tristimulus values to the output device 300. The color processing device 100B then ends the color processing.

In the above embodiment illustrated in FIG. 7 and FIG. 8, the color processing device 100B expresses the color vision of a person by Expression (8) to Expression (10) by weighted addition of the color vision of the P-type color vision, the D-type color vision, or the T-type color vision and the color vision of the person with a normal color vision using the color vision strength of each of the P-type color vision, the D-type color vision, and the T-type color vision. Thus, the color processing device 100B can execute the color processing according to the type of color vision and the color vision strength with higher accuracy than before.

When creating a printed matter including sentences of color characters or the like and images, a map used in navigation, or the like, the color processing device 100B can simulate in advance how the printed matter, map or the like looks according to the type of color vision. Thus, the color processing device 100B can create, more easily than before, the printed matter, map or the like which is easily recognized by persons of various kinds of color vision, by adjusting the arrangement of colors, brightness or the like according to the result of the simulation. Further, the color processing device 100B can understand the way of viewing of persons of various types of color vision based on the result of the simulation, and can improve the communication.

Further, the color processing device 100B executes the transformation processing on the image, map or the like so that when the person of the P-type color vision views it, the person of the P-type color vision senses the color difference sensed by the person with a normal color vision, whereby the person of the P-type color vision or the like can easily distinguish colors in the image, map or the like displayed on the display or the like or printed by the printer or the like.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. A non-transitory computer-readable medium storing instructions that, when executed by a computer, cause the computer to execute processing of:
   transforming a first color information indicating a first color in a first color space into a second color information in a second color space which is an opponent color space different from the first color space, according to a type of a color vision and a color vision strength indicating a degree of the color vision;
   calculating, in the second color space, a third color information having a predetermined color difference with respect to the transformed second color information; and
   transforming the calculated third color information into a fourth color information indicating a second color in the first color space, according to a type of a color vision and a color vision strength indicating a degree of the color vision.

2. The non-transitory computer-readable medium according to claim 1, the processing further comprising processing of acquiring determination information indicating a result of determination by a subject of whether the first color and the second color are different or not, wherein
   the processing of transforming into the fourth color information transforms the third color information into the fourth color information by changing the color vision strength according to the determination information.

3. The non-transitory computer-readable medium according to claim 1, wherein
   the processing of calculating the third color information calculates the third color information by changing at least one component of a plurality of components included in the second color information.

4. The non-transitory computer-readable medium according to claim 1, wherein
the second color space is an ATD space.

5. The non-transitory computer-readable medium according to claim 4, wherein
the processing of calculating the third color information calculates the third color information by changing at least a T component or a D component of an A component, the T component, and the D component which are included in the second color information.

6. A color sense inspection system, comprising:
a processing device executing processing of transforming a first color information indicating a first color in a first color space into a second color information in a second color space which is an opponent color space different from the first color space, according to a type of a color vision and a color vision strength indicating a degree of the color vision; calculating, in the second color space, a third color information having a predetermined color difference with respect to the transformed second color information; and transforming the calculated third color information into a fourth color information indicating a second color in the first color space, according to a type of a color vision and a color vision strength indicating a degree of the color vision;
an output device outputting the first color and the second color in contrast to each other; and
an input device accepting a result of a determination of a comparison between the first color and the second color by a subject.

7. The color sense inspection system according to claim 6, wherein
the second color space is an ATD space.

8. An output system, comprising:
a processing device executing processing of transforming a first color information indicating a first color in a first color space into a second color information in a second color space which is an opponent color space different from the first color space, according to a first type of a color vision and a first color vision strength indicating a degree of the color vision; and transforming the second color information into a third color information indicating a second color in the first color space, according to a second type of a color vision and a second color vision strength; and
an output device outputting the second color in place of the first color.

9. The output system according to claim 8, wherein
1) the first type and the second type are different and the first color vision strength and the second color vision strength are different, 2) the first type and the second type are the same and the first color vision strength and the second color vision strength are different, or 3) the first type and the second type are different and the first color vision strength and the second color vision strength are the same.

10. The output system according to claim 8, wherein
information indicating a person with a normal color vision is used for the first type and the first color vision strength or the second type and the second color vision strength.

11. The output system according to claim 8, wherein
the second color space is an ATD space.

12. A color vision correction image processing system, comprising the output system according to any claim 8.

13. A color vision simulation image processing system, comprising the output system according to claim 8.

* * * * *